United States Patent
Lu et al.

(10) Patent No.: US 8,709,795 B2
(45) Date of Patent: Apr. 29, 2014

(54) LIGHT TRANSFORMATION PARTICLE AND PHOTOBIOREACTOR

(75) Inventors: Wen-Chang Lu, Hsinchu (TW); Chung-Cheng Han, Taipei (TW); Yun-Huin Lin, Hsinchu (TW); Hom-Ti Lee, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 1031 days.

(21) Appl. No.: 12/700,272

(22) Filed: Feb. 4, 2010

(65) Prior Publication Data

US 2011/0111490 A1   May 12, 2011

(30) Foreign Application Priority Data

Nov. 9, 2009   (TW) ................ 98137889 A

(51) Int. Cl.
  *C12M 1/00*  (2006.01)
  *C09K 11/02*  (2006.01)

(52) U.S. Cl.
  USPC ... 435/292.1; 435/257.1; 47/1.4; 252/301.36; 252/301.4 R

(58) Field of Classification Search
  USPC .................. 435/257.1, 292.1; 47/1.4
  See application file for complete search history.

(56) References Cited

U.S. PATENT DOCUMENTS

| | | | |
|---|---|---|---|
| 4,253,271 A | 3/1981 | Raymond | |
| 4,952,511 A | 8/1990 | Radmer | |
| 5,104,803 A | 4/1992 | Delente | |
| 5,151,368 A | 9/1992 | Brimhall et al. | |
| 5,162,051 A | 11/1992 | Hoeksema | |
| 5,443,985 A | 8/1995 | Lu et al. | |
| 5,643,674 A * | 7/1997 | Bruno et al. | 428/403 |
| 5,958,761 A | 9/1999 | Yogev et al. | |
| 6,492,149 B1 | 12/2002 | Muller-Feuga | |
| 6,509,188 B1 | 1/2003 | Trösch et al. | |
| 6,602,703 B2 | 8/2003 | Dutil | |
| 6,649,946 B2 | 11/2003 | Bogner et al. | |
| 6,724,142 B2 | 4/2004 | Ellens et al. | |
| 6,815,204 B2 | 11/2004 | Muller-Feuga et al. | |
| 7,258,816 B2 | 8/2007 | Tamaki et al. | |
| 7,297,293 B2 | 11/2007 | Tamaki et al. | |
| 2004/0048364 A1 | 3/2004 | Trosch | |

(Continued)

FOREIGN PATENT DOCUMENTS

| | | |
|---|---|---|
| EP | 0 239 272 A2 | 9/1987 |
| JP | 4-287678 A | 10/1992 |

(Continued)

OTHER PUBLICATIONS

English language machine translation of WO 03/064557 (Aug. 7, 2003), pp. 1-3.*

(Continued)

*Primary Examiner* — William H Beisner
(74) *Attorney, Agent, or Firm* — Birch, Stewart, Kolasch & Birch, LLP

(57) ABSTRACT

A light transformation particle is provided. The light transformation particle of the invention includes a light-shifting layer containing at least one light-emitting material, wherein the light-emitting layer transforms ultraviolet light, yellow-green light, or infrared light to red-orange light or blue-violet light. The light transformation particle further includes a core layer and/or a shell layer. The present invention further provides a photobioreactor containing the light transformation particle of the invention.

26 Claims, 4 Drawing Sheets

(56) References Cited

U.S. PATENT DOCUMENTS

| | | |
|---|---|---|
| 2005/0239182 A1 | 10/2005 | Berzin |
| 2008/0160591 A1 | 7/2008 | Willson et al. |
| 2009/0181438 A1* | 7/2009 | Sayre .......................... 435/134 |

FOREIGN PATENT DOCUMENTS

| | | |
|---|---|---|
| JP | 10-98964 A | 4/1998 |
| JP | 11-266727 A | 10/1999 |
| TW | 562739 B | 11/2003 |
| TW | 200740958 A | 11/2007 |
| TW | 200809283 A | 2/2008 |
| WO | WO 03064557 A1 * | 8/2003 |
| WO | WO-2005/006838 A2 | 1/2005 |
| WO | WO-2008/005926 A2 | 1/2008 |
| WO | WO-2009/017677 A2 | 2/2009 |
| WO | WO-2009/018498 A2 | 2/2009 |
| WO | WO-2009/069967 A2 | 6/2009 |

OTHER PUBLICATIONS

Richmond, "Principles for attaining maximal microalgal productivity in photobioreactors: an overview", Hydrobiologia, 512, 2004, pp. 33-37.

Barbosa et al., "Microalgae Cultivation in Air-Lift Reactors: Modeling Biomass Yield and Growth Rate as a Function of Mixing Frequency", Food and Bioprocess Engineering Group, Wageningen University, 2003, pp. 171-179.

* cited by examiner

LIGHT TRANSFORMATION PARTICLE AND PHOTOBIOREACTOR

CROSS REFERENCE TO RELATED APPLICATIONS

This application claims priority of Taiwan Patent Application No. 098137889, filed on Nov. 9, 2009, the entirety of which is incorporated by reference herein.

BACKGROUND OF THE INVENTION

1. Field of the Invention

The present invention relates to a photosynthetic system, and in particular relates to a light transformation particle for increasing the photosynthetic efficiency of living organisms.

2. Description of the Related Art

An autotrophic organism, like algae, can absorb carbon dioxide in the atmosphere. It has the potential to decrease greenhouse gases and hinder the greenhouse effect. Also, algae may be used to develop bio-fuel. Photosynthetic system can be used to breed algae by using carbon dioxide and light energy. The GreenFuel Company and the APS (Arizona Public Service) Company has achieved algae breeding systems utilizing $CO_2$ from power plants. The systems demonstrate that algae can be used to decrease $CO_2$ in the atmosphere.

A tubular photobioreactor is the most popular type of photobioreactor because it has advantages such as high transmission, low cycle time, and simple operation. In the tubular photobioreactor, a light source is located at the outside of the reactor to provide a light energy for growing algae. However, the photosynthesis efficiency of the tubular photobioreactor is poor, because the light energy is unequally distributed over the reactor. For example, portions near the tube wall are exposed to excessive light energy, but other portions lack exposure.

In order to solve the problem of the uneven illumination, an artificial light or LED is used. In the photobioreactor, an LED is used to replace sunlight, and is spirally arranged on an axle to increase light utilization. The use of LEDs improves the growth of algae, wherein the algae grows 3 times its original size every 24-48 hours. However, use of LEDs requires additional power sources and is inappropriate for a large scale cultivation.

Thus, a novel photobioreactor is required to circumvent the previously mentioned problems.

BRIEF SUMMARY OF THE INVENTION

The invention provides a light transformation particle, comprising a light-shifting layer containing at least one light-emitting material, wherein the light-emitting material layer transforms ultraviolet light, yellow-green light, or infrared light to red-orange light or blue-violet light.

The invention also provides a light transformation particle, comprising a core layer and a light-shifting layer coated on the core layer. The light-shifting layer contains at least one light-emitting material. The light-emitting material layer transforms ultraviolet light, yellow-green light, or infrared light to red-orange light or blue-violet light, and a shell layer is coated on the light-shifting layer.

The invention further provides a photobioreactor, comprising a fluid, a photosynthetic organism, a carbon source, a light source, and a plurality of light transformation particles of the invention. The fluid, photosynthetic organism, carbon source, and light transformation particles are placed in a reactor.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The light transformation particle of the invention comprises a core layer, a light-shifting layer, and a shell layer, wherein the light-shifting layer is a necessary layer, and the core layer and shell layer are optionally applied. The light transformation particle has a diameter of about 0.3 to 10 mm.

The light-shifting layer comprises at least one light-emitting material, wherein the light-emitting material transforms ultraviolet light, yellow-green light, or infrared light to red-orange light or blue-violet light, and the energy gap of the light-emitting material is less than 1.9 ev, or more than 3.1 ev.

The light-emitting material includes, but is not limited to, a fluorescent material, a phosphorescent material, a wavelength conversion material, or a long afterglow material. Example of the light-emitting material may be calcium sulfide, barium-magnesium aluminate, or yttrium oxysulfide.

The term "ultraviolet light" is used herein to refer to ultraviolet A in the wavelength range of 320-400 nm, ultraviolet B in the wavelength range of 290-320 nm, and ultraviolet C in the wavelength range of 200-280 nm.

The term "yellow-green light" is used herein to refer to a light in the wavelength range of 550-590 nm.

The term "infrared light (IR)" is used herein to refer to near IR in the wavelength range of 700-2000 nm, middle IR in the wavelength range of 3000-5000 nm, and far IR in the wavelength range of 8000-14000 nm.

The term "red-orange light" is used herein to refer to a light in the wavelength range of 600-750 nm, and the term "blue-violet light" is used herein to refer to a light in the wavelength range of 380-470 nm.

Figure 1:
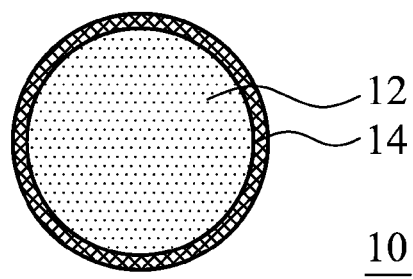
FIG. 1 shows a light transformation particle according to an embodiment of the invention.

In one embodiment, the light transformation particle of the invention comprises a core layer and a light-shifting layer. Referring to FIG. 1, the light transformation particle 10 includes a core layer 12 and a light-shifting layer 14, wherein the light-shifting layer 14 is formed on surface of the core layer 12.

The core layer 12 includes, but is not limited to, montmorillonite clay (e.g., pure montmorillonite clay, sodium or calcium montmorillonite clay, organic or inorganic intercalated montmorillonite clay, or crosslinked montmorillonite clay), quartz, kaolin, pyrophyllite, diatomite, alkaline earth metal oxides or hydroxide, $Al_2O_3$, $SiO_2$, $Cu_2O_2$, or combinations thereof. In one embodiment, the core layer 12 comprises $((Na, Ca)_{0.33}(Al,Mg)_2[Si_4O_{10}](OH)_2 \cdot nH_2O)$, and its functional group(s) are able to absorb ultraviolet light and far IR (e.g., asymmetric vibration (1037 $cm^{-1}$) of Si—O). In addition, dependant upon the decrease of the core layer 12, red-shift or blue-shift phenomenon of excitation or emission may occur to expand the wavelength bandwidth of the light transformation particle.

The core layer 12 may be a solid or hollow particle, and density of the core layer 12 can be adjusted in accordance with its composition and pore volume.

One or more light-emitting materials are coated on a surface of the core layer 12 to form a light-shifting layer 14. The coating methods of the light-emitting material are well known in the art. For example, one skilled in the art would select an appropriate method, such as a coating, electroplating, electroless plating, evaporation, printing, or vacuum coating method.

Figure 2:
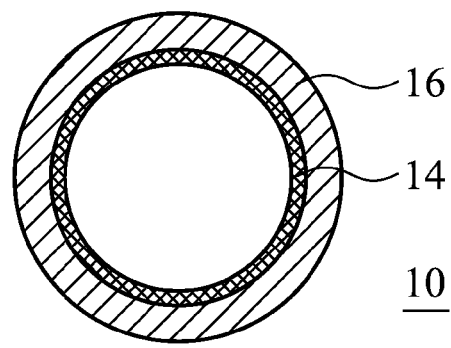
FIG. 2 shows a light transformation particle according to another embodiment of the invention.

In another embodiment, the light transformation particle of the invention comprises a light-shifting layer and a shell layer. Referring to FIG. 2, the light transformation particle 10 includes a light-shifting layer 14 and a shell layer 16, wherein the shell layer 16 is coated on the outer surface of the light-shifting layer 14. In this embodiment, the light-shifting layer 14 is coated on the inner surface of the shell layer 16.

The shell layer 16, preferably, has high intensity, hardness, and transmittance. The material of the shell layer 16 includes, but is not limited to, poly(methyl methacrylate), a metal oxide, a silicon dioxide, a titanium dioxide, a glass (borosilicate glass, a phosphosilicate glass, or a alkali glass), or combinations thereof.

Further, in order to increase light-shifting efficiency, a compatible compound may be coated on or doped in the shell layer 16 to increase the energy gap thereof. The compatible compound can increase the shifted photon to improve luminous efficiency of the light transformation particle 10. For example, selenium sulfide (SeS, energy gap: 3.7 ev), a selenium sulfide transparent film or a nano-particle, can be added to the shell layer zinc sulfide (ZnS) to increase the energy gap of the shell layer 16. In other words, the shell layer 16 preferably has a larger energy gap than the light-shifting layer 14.

Examples of the compatible compound include, but are not limited to, magnesium oxide, zinc oxide, or magnesium sulfide.

Figure 3:
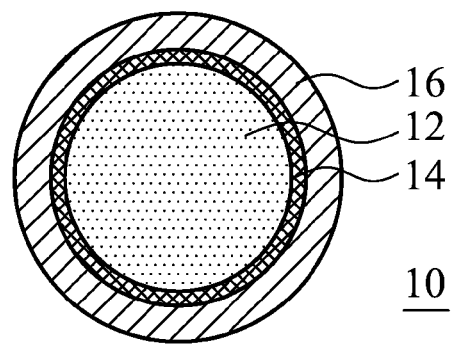
FIG. 3 shows a light transformation particle according to another embodiment of the invention.

In another embodiment, the light transformation particle of the invention further comprises a core layer 12, a light-shifting layer 14, and a shell layer 16, as shown in FIG. 3. The material of the core layer 12, light-shifting layer 14, and shell layer 16 are mentioned above. Even if the core layer 12 is solid as shown in FIG. 3, the core layer 12 also can be changed to have a hollow structure.

The invention further provides a photobioreactor. The photobioreactor comprises a fluid, a photosynthetic organism, a carbon source, a light source, and a plurality of light transformation particles of the invention, wherein the fluid, photosynthetic organism, carbon source, and light transformation particles are placed in a reactor.

Figure 4:
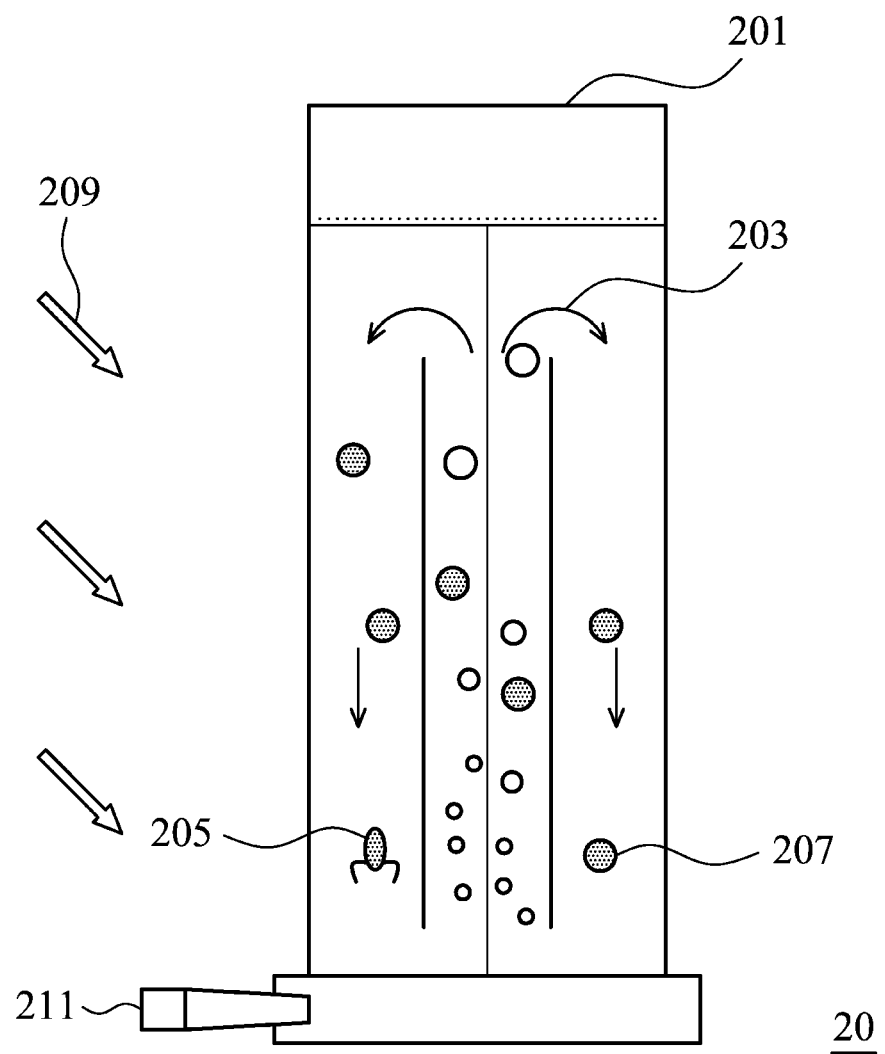
FIG. 4 shows a photoreactor according to an embodiment of the invention.

FIG. 4 illustrates an embodiment of photobioreactor of the invention. It should be understood that the drawings herein are made in simplicity, and are utilized for illustrating associated elements related to the invention. In practical usage however, the photobioreactor is more complexly structured.

Referring to FIG. 4, a photobioreactor 20 comprises a closed reactor 201 containing fluid 203, photosynthetic organism 205, and light transformation particles 207 of the invention. The fluid 203 includes, but is not limited to, fresh water, seawater, wastewater, or any fluid which is capable of growing photosynthetic organisms.

The term "photosynthetic organism" is used herein to refer to an autotroph containing chloroplast and/or chlorophyll. Examples of photosynthetic organisms include, but is not limited to, a plant, an alga, a bacterium, etc., preferably, alga.

In order to obtain a preferred photosynthetic response, one skilled in the art may select a suitable fluid 203 and light transformation particles 207 depending on the photosynthetic organism 205. In one embodiment, the fluid 203 can further comprise nitrogen, phosphorous, potassium or other materials which improve the growth of a photosynthetic organism. In another embodiment, the light transformation particles 207 can emit a light with a specific wavelength, such as 435 mm, 620 mm and/or 675 mm depending on the excitation spectrum of the photosynthetic organism 205.

The light source 209 can be sunlight or an artificial light, such as red LED light, but LED light, UV and/or IR, preferably, sunlight. The artificial light can be located inside and/or outside of the reactor 201.

The carbon source 211 usually refers to carbon dioxide. In FIG. 4, the carbon dioxide is injected into the reactor 201 by a pump. One skilled in the art would select appropriate methods or equipment to inject carbon dioxide to the reactor 201 and remove the oxygen within the reactor 201 for practical use.

In the photobioreactor of the invention, the light transformation particles 207 can effectively transform the light source 209 to a specific absorption spectrum for algae (e.g., 400 to 700 nm). The light transformation particles 207 are also mobile in the reactor 201 to increase the photic zone. In addition, the light transformation particles 207 can attach and collide with the side wall of the reactor 201 to remove the dirt on the inner surface of the reactor 201, so that the reactor 201 has excellent transmittance.

EXAMPLE

Example 1

Barium-Magnesium Aluminate Powders 10.86 g of barium carbonate, 0.56 g of magnesium oxide, and 1.57 g of manganese carbonate were dissolved in 45 ml nitric acid, sequentially, and then mixed to form a nitrate solution. The nitrate solution was added to an aluminum nitrate $(Al(NO_3)_3 \cdot 9H_2O)$ solution and reacted with 0.1 mol/L citrate (4.2 g) serving as a chelating agent. Next, the mixture were heated and mixed until block gels were formed. The block gels were dried and grinded to a powdered form and then the powder was sintered at 1200° C. for 3.5 hours at a high temperature furnace to obtain the barium-magnesium aluminate powder.

The excitation and emission spectra of the barium-magnesium aluminate powder were determined by an SPE Fluor Max spectrometer with an operating range of 200 to 900 nm. The results are shown in FIG. 5.

Figure 5:
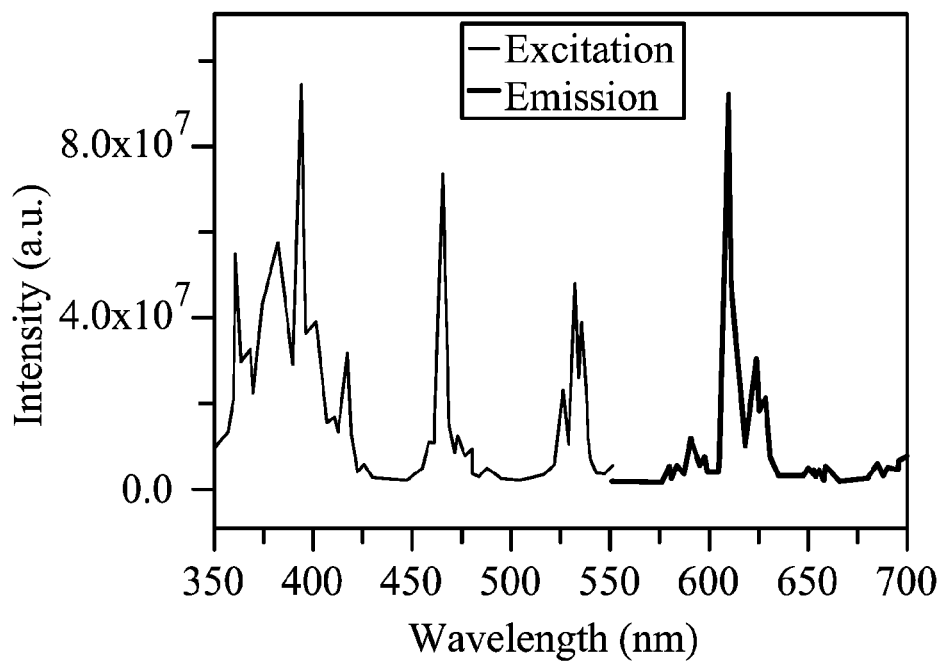
FIG. 5 shows the excitation and emission spectra of the barium-magnesium aluminate powder of the invention.

Referring to FIG. 5, the barium-magnesium aluminate powders transformed excitation light of 350-550 nm to red light of 600-650 nm.

Example 2

Eu(Ba)$_3$Phen Powder 5 ml of hydrochloric acid (36%) was slowly dropped into a mixture (0.5 mmol) of europium oxide and lanthanum oxide (1:0.05), and the mixture was dissolved to form a rare earth solution with a pH value of 4-5, and then heated to remove the water and hydrogen chloride. Next, the filtrated and washed with anhydrous methanol, and dried to obtain EuCl$_3$ and LaCl$_3$. The 1-benzoylphosphine oxide, ammonia, triphenylphosphine oxide, EuCl$_3$ and LaCl$_3$ were added to methanol by a ration of 3:3:1:1:0.05, mixed at 20-60° C. for 2 hours, and then filtrated and washed with anhydrous methanol to obtain the Eu(Ba)$_3$phen powder.

The excitation and emission spectra of the Eu(Ba)$_3$phen powders were determined by an SPE Fluor Max spectrometer with an operating range of 200 to 900 nm. The results are shown in FIG. 6.

Figure 6:
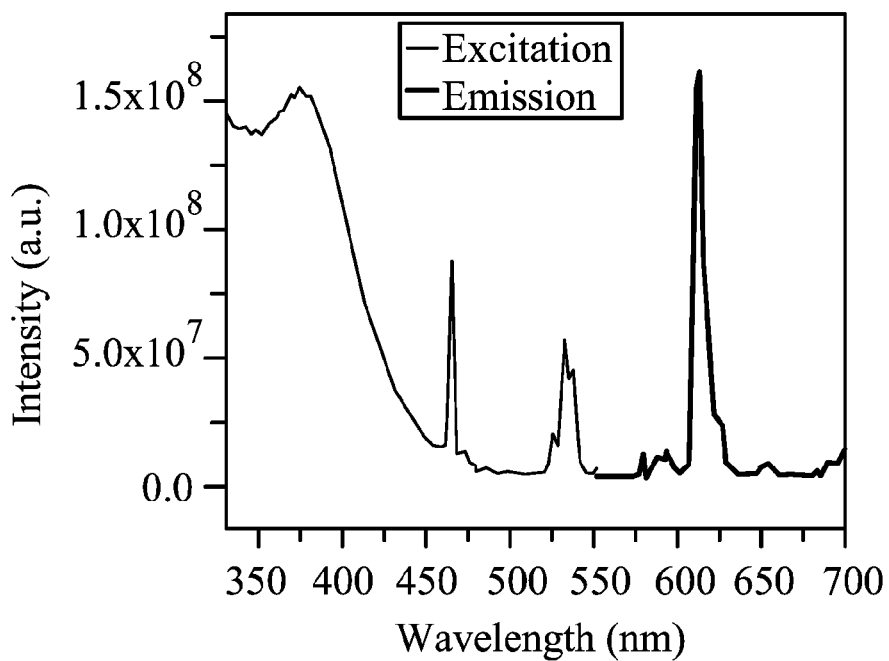
FIG. 6 shows the excitation and emission spectra of the $Eu(Ba)_3phen$ powder of the invention.

Referring to FIG. 6, the Eu(Ba)$_3$phen powders transformed excitation light of 350-550 nm to red light of 600-650 nm.

Example 3

Light Transformation Particle of Barium-Magnesium Aluminate

The barium-magnesium aluminate powders of example 1 were coated on montmorillonite powder with a diameter of 3-5 mm, and soaked on the sodium silicate solution (Na$_2$SiO$_3$) to obtain the light transformation particles of barium-magnesium aluminate, wherein the sodium silicate solution was used to form the shell layer. The excitation and emission spectra of the light transformation particle were determined by an SPE Fluor Max spectrometer with excitation wavelength of 396 nm. The results are shown in FIG. 7.

Figure 7:
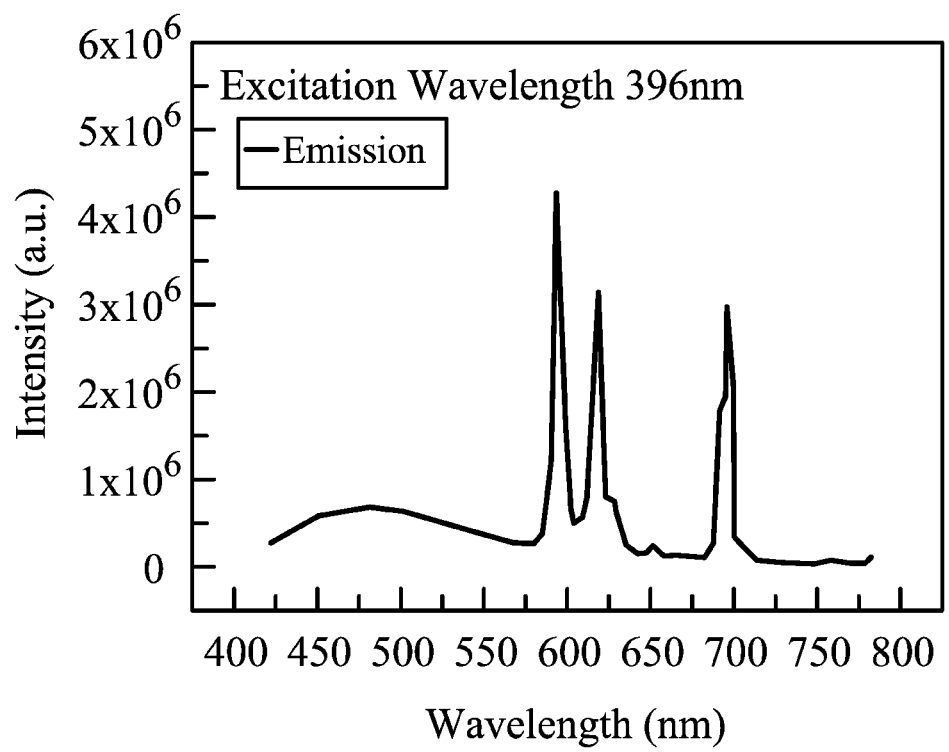
FIG. 7 shows the excitation and emission spectra of the light transformation particle of the barium-magnesium aluminate.

Referring to FIG. 7, the light transformation particles transformed excitation light of 396 nm to red light of 600-700 nm.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A light transformation particle, comprising:
a light-shifting layer containing at least one light-emitting material; and
a core layer,
wherein the light-shifting layer is formed on the core layer, and the core layer comprises a montmorillonite clay, a quartz, a kaolin, a pyrophyllite, a diatomite, or combinations thereof.

2. The light transformation particle as claimed in claim 1, wherein the light transformation particle has a diameter of 0.3 to 10 mm.

3. The light transformation particle as claimed in claim 1, wherein the light-emitting material comprises a fluorescent material, a phosphorescent material, a wavelength conversion material, or a long afterglow material.

4. The light transformation particle as claimed in claim 1, wherein an energy gap of the light-emitting material is less than 1.9 ev, or more than 3.1 ev.

5. The light transformation particle as claimed in claim 1, wherein the montmorillonite clay comprises a pure montmorillonite clay, a sodium or calcium montmorillonite clay, an organic or inorganic intercalated montmorillonite clay, or a crosslinked montmorillonite clay.

6. The light transformation particle as claimed in claim 1, further comprising a shell layer coated on the light-shifting layer.

7. The light transformation particle as claimed in claim 6, wherein the shell comprises a poly(methyl methacrylate), a metal oxide, a silicon dioxide, a titanium dioxide, a glass, or combinations thereof.

8. The light transformation particle as claimed in claim 7, wherein the glass comprises a borosilicate glass, a phosphosilicate glass, or a alkali glass.

9. The light transformation particle as claimed in claim 6, wherein the shell layer further comprises a compound for increasing the energy gap of the shell layer.

10. The light transformation particle as claimed in claim 9, wherein the compound comprises a magnesium oxide, a magnesium sulfide, a zinc oxide, a strontium oxide or a aluminum oxide.

11. The light transformation particle as claimed in claim 9, wherein the energy gap of the shell layer is larger than the energy gap of the light-shifting layer.

12. The light transformation particle as claimed in claim 1, wherein the light-emitting material layer transforms ultraviolet light, yellow-green light, or infrared light to red-orange light or blue-violet light.

13. A photobioreactor, comprising:
a fluid;
a photosynthetic organism;
a carbon source;
a light source, and
a plurality of light transformation particles as claimed in claim 1, wherein the fluid, photosynthetic organism, carbon source, and light transformation particles are placed in a reactor.

14. The photobioreactor as claimed in claim 13, wherein the photosynthetic organism is an alga.

15. The photobioreactor as claimed in claim 13, wherein the carbon source is carbon dioxide.

16. The photobioreactor as claimed in claim 13, wherein the light source is sunlight.

17. The photobioreactor as claimed in claim 13, wherein the light transformation particles are separated in the reactor.

18. A light transformation particle, comprising:
a core layer, wherein the core layer comprises a montmorillonite clay, quartz, kaolin, pyrophyllite, diatomite, or combinations thereof;
a light-shifting layer coated on the core layer, wherein the light-shifting layer contains at least one light-emitting material; and
a shell layer coated on the light-shifting layer.

19. The light transformation particle as claimed in claim 18, wherein the light transformation particle has a diameter of 0.3 to 10 mm.

20. The light transformation particle as claimed in claim 18, wherein the light-emitting material comprises a fluorescent material, a phosphorescent material, a wavelength conversion material, or a long afterglow material.

21. The light transformation particle as claimed in claim 18, wherein an energy gap of the light-emitting material is less than 1.9 ev, or more than 3.1 ev.

22. The light transformation particle as claimed in claim 18, wherein the montmorillonite clay comprises a pure montmorillonite clay, a sodium or calcium montmorillonite clay, an organic or inorganic intercalated montmorillonite clay, or a crosslinked montmorillonite clay.

23. The light transformation particle as claimed in claim 18, wherein the shell layer further comprises a compound for increasing the energy gap of the shell layer.

24. The light transformation particle as claimed in claim 23, wherein the compound comprises a magnesium oxide, a magnesium sulfide, a zinc oxide, a strontium oxide or a aluminum oxide.

25. The light transformation particle as claimed in claim 23, wherein the energy gap of the shell layer is larger than the energy gap of the light-shifting layer.

26. The light transformation particle as claimed in claim 18, wherein the light-emitting material layer transforms ultraviolet light, yellow-green light, or infrared light to red-orange light or blue-violet light.

* * * * *